(12) United States Patent
Kwon et al.

(10) Patent No.: US 11,969,260 B2
(45) Date of Patent: Apr. 30, 2024

(54) APPARATUS AND METHOD FOR DETECTING BODY COMPONENT

(71) Applicant: SAMSUNG ELECTRONICS CO., LTD., Suwon-si (KR)

(72) Inventors: Yong Joo Kwon, Yongin-si (KR); Yeol Ho Lee, Anyang-si (KR); Joon Hyung Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 475 days.

(21) Appl. No.: 17/237,862

(22) Filed: Apr. 22, 2021

(65) Prior Publication Data
US 2022/0160303 A1 May 26, 2022

(30) Foreign Application Priority Data
Nov. 20, 2020 (KR) .................. 10-2020-0156232

(51) Int. Cl.
*A61B 5/145* (2006.01)
*A61B 5/00* (2006.01)
*A61B 90/00* (2016.01)

(52) U.S. Cl.
CPC ........ *A61B 5/6843* (2013.01); *A61B 5/14532* (2013.01); *A61B 5/14546* (2013.01); *A61B 5/4845* (2013.01); *A61B 5/4872* (2013.01); *A61B 5/4875* (2013.01);
(Continued)

(58) Field of Classification Search
CPC ..... A61B 5/02; A61B 5/02416; A61B 5/1455; A61B 5/14551; A61B 5/14552; A61B 5/6843; A61B 5/14532; A61B 5/14546; A61B 5/4845; A61B 5/4872; A61B 5/4875; A61B 5/7239; A61B 5/7203; A61B 5/725
See application file for complete search history.

(56) References Cited

U.S. PATENT DOCUMENTS

| 6,083,171 A | 7/2000 | Ono et al. |
| 8,216,152 B2 | 7/2012 | Tanaka et al. |
| 2014/0257050 A1 | 9/2014 | Kuroda et al. |

(Continued)

FOREIGN PATENT DOCUMENTS

| JP | 3211130 B2 | 9/2001 |
| JP | 3462251 B2 | 11/2003 |

(Continued)

OTHER PUBLICATIONS

Chandrasekhar et al., "Smartphone-based blood pressure monitoring via the oscillometric finger-pressing method," Science Translational Medicine, vol. 10, eaap8674, 2018, Total 12 pages.

*Primary Examiner* — Chu Chuan Liu
(74) *Attorney, Agent, or Firm* — Sughrue Mion, PLLC

(57) ABSTRACT

An apparatus for detecting a body component according to an example embodiment includes: a sensor configured to detect a bio-signal of an object according to a contact pressure that gradually changes between the object and the sensor; and a processor configured to determine a time point, at which an amplitude of an alternating current (AC) component of the bio-signal is maximum or a slope of a direct current (DC) component of the bio-signal is maximum, and to detect a body component of the object based on the determined time point.

19 Claims, 20 Drawing Sheets

(52) U.S. Cl.
CPC .......... *A61B 5/7214* (2013.01); *A61B 5/7239* (2013.01); *A61B 2090/065* (2016.02)

(56) References Cited

U.S. PATENT DOCUMENTS

| | | |
|---|---|---|
| 2017/0367659 A1 | 12/2017 | Lading et al. |
| 2018/0070837 A1 | 3/2018 | Huijbregts et al. |
| 2018/0310838 A1* | 11/2018 | Jeon ........................ A61B 5/024 |
| 2019/0104997 A1* | 4/2019 | Kang ................... A61B 5/6826 |
| 2019/0110758 A1* | 4/2019 | Kang ................... A61B 5/6831 |
| 2020/0008693 A1 | 1/2020 | Mukkamala et al. |
| 2020/0237241 A1* | 7/2020 | Koppel .............. A61B 5/02416 |

FOREIGN PATENT DOCUMENTS

| | | |
|---|---|---|
| JP | 5146994 B2 | 2/2013 |
| JP | 5958222 B2 | 7/2016 |
| WO | 2017/169786 A1 | 10/2017 |

\* cited by examiner

APPARATUS AND METHOD FOR DETECTING BODY COMPONENT

CROSS-REFERENCE TO RELATED APPLICATION(S)

This application claims priority from Korean Patent Application No. 10-2020-0156232, filed on Nov. 20, 2020, in the Korean Intellectual Property Office, the entire disclosure of which is herein incorporated by reference for all purposes.

BACKGROUND

1. Field

Example embodiments of the disclosure relate to an apparatus and a method for non-invasively detecting a body component.

2. Description of Related Art

Generally, when bio-signals are detected by a detector for non-invasively detecting bio-signals using light, ultrasonic waves, impedance, etc., contact pressure between a body part and the detector needs to be maintained at a constant level.

However, local blood pressure of a body part may be generally changed due to a change in blood pressure of the central artery and/or a change in hydrostatic pressure, and a volume of blood vessels in the body part may be changed accordingly, thereby causing a change in a volume ratio between the internal body tissue and the blood vessels, and affecting accuracy of a non-invasive detection of a bio-signal.

SUMMARY

According to an aspect of an example embodiment, there is provided an apparatus for detecting a body component, the apparatus including: a sensor configured to detect a bio-signal of an object according to a contact pressure that gradually changes between the object and the sensor; and a processor configured to determine a time point, at which an amplitude of an alternating current (AC) component of the bio-signal is maximum or a slope of a direct current (DC) component of the bio-signal is maximum, and to detect a body component of the object based on the determined time point.

The processor may be further configured to perform filtering on the amplitude of the AC component or the slope of the DC component, to remove outlier data.

The processor may be further configured to perform filtering on the bio-signal to remove noise in the contact pressure, and differentiate the filtered bio-signal, and the processor may be further configured to detect a point having a value greater than a first predetermined threshold value, or a point having a value equal to or less than a second predetermined threshold, from the differentiated bio-signal, and prior to determining the time point, remove an amplitude value of the filtered bio-signal at the detected point.

Based on a detection of a plurality of time points, at which the amplitude of the AC component or the slope of the DC component in the bio-signal is greater than or equal to a predetermined threshold, the processor may be further configured to correct the amplitude of the AC component or the slope of the DC component.

The processor may be further configured to correct an amplitude value of the AC component or a slope value of the DC component by obtaining a moving average of the amplitude value of the AC component or the slope value of the DC component in units of predetermined intervals.

The sensor may further include a contact pressure measuring sensor configured to measure the contact pressure between the object and the sensor.

The apparatus may further include an output interface configured to output at least one of guide information for guiding a change in the contact pressure, which is generated by the processor, and the contact pressure measured by the contact pressure measuring sensor.

The processor may be further configured to generate an amplitude graph of the AC component of the bio-signal with respect to the measured contact pressure, and determine the time point, at which the amplitude of the AC component is maximum, by using the amplitude graph.

The processor may be further configured to generate a slope graph of the DC component of the bio-signal with respect to the measured contact pressure, and determine the time point, at which the slope of the DC component is maximum, by using the slope graph.

The processor may be further configured to determine the time point, at which the amplitude of the AC component or the slope of the DC component is maximum, with respect to the measured contact pressure that is within a reference contact pressure range, the reference contact pressure range being set for a user of the object.

The processor may be further configured to extract a feature value from the bio-signal based on the determined time point, and detect the body component based on the feature value.

The feature value may include at least one of the contact pressure, an amplitude value of the AC component, and a slope value of the DC component corresponding to the time point at which the amplitude of the AC component of the bio-signal is maximum or the time point at which the slope of the DC component of the bio-signal is maximum.

The body component may include at least one of triglyceride, blood glucose, electrolyte, carotenoid, body water, body fat, protein, and alcohol.

According to an aspect of an example embodiment, there is provided a method of detecting a body component, the method including: detecting a bio-signal from an object based on a contact pressure that gradually changes between the object and a sensor; determining a time point at which an amplitude of an alternating current (AC) component of the bio-signal is maximum or a slope of a direct current (DC) component of the bio-signal is maximum; and detecting a body component based on the determined time point.

The determining the time point may include performing filtering on the amplitude of the AC component or the slope of the DC component, to remove outlier data.

The determining the time point may include performing filtering on the bio-signal to remove noise in the contact pressure; differentiating the filtered bio-signal, and detecting a point having a value greater than a first predetermined threshold value, or a point having a value equal to or less than a second predetermined threshold, from the differentiated bio-signal; and prior to determining the time point, removing an amplitude value of the filtered bio-signal at the detected point.

The determining the time point may include, based on a detection of a plurality of time points, at which the amplitude of the AC component or the slope of the DC component in the bio-signal is greater than or equal to a predetermined threshold, correcting the amplitude of the AC component or the slope of the DC component.

The correcting may include correcting an amplitude value of the AC component or a slope value of the DC component by obtaining a moving average of the amplitude value of the AC component or the slope value of the DC component in units of predetermined intervals.

The detecting the bio-signal may include measuring the contact pressure between the object and the sensor.

The determining the time point may include generating an amplitude graph of the AC component of the bio-signal with respect to the measured contact pressure, and determining the time point, at which the amplitude of the AC component is maximum, by using the amplitude graph.

The determining the time point may further include generating a slope graph of the DC component of the bio-signal with respect to the measured contact pressure, and determining the time point, at which the slope of the DC component is maximum, by using the slope graph.

BRIEF DESCRIPTION OF THE DRAWINGS

The above and/or other aspects will be more apparent by describing certain example embodiments, taken in conjunction with the accompanying drawings, in which.

DETAILED DESCRIPTION

Figure 1:
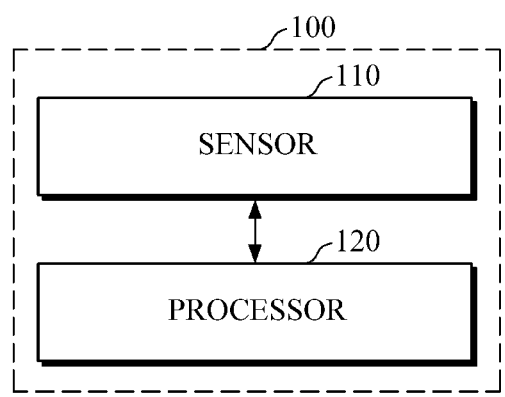
FIG. 1 is a block diagram illustrating an apparatus for detecting a body component according to an example embodiment.

Details of example embodiments are included in the following detailed description and drawings. Advantages and features of the disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof.

Hereinafter, example embodiments of an apparatus and a method for detecting a body component will be described in detail with reference to the accompanying drawings. The apparatus for detecting a body component may be mounted in medical devices of specialized medical institutions, in wearable devices, such as a smart watch worn on the wrist, a smart band type wearable device, a headphone type wearable device, a headband type wearable, etc., or in mobile devices such as a smartphone, a tablet PC, etc., but is not limited thereto.

FIG. 1 is a block diagram illustrating an apparatus for detecting a body component according to an example embodiment.

Referring to FIG. 1, the apparatus 100 for detecting a body component includes a sensor 110 and a processor 120.

The sensor 110 may come into contact with an object, and may detect a bio-signal of the object according to contact pressure. The sensor 110 may include a pulse wave sensor for detecting a pulse wave signal including a photoplethysmography (PPG) signal. However, the sensor 110 is not limited thereto, and may include an ultrasonic sensor, an impedance sensor, and the like. For convenience of explanation, the following description will be focused on a pulse wave sensor.

The sensor 110 may include one or more light sources for emitting light onto an object, and one or more detectors for detecting light scattered or reflected from the object. The light source may include a light emitting diode (LED), a laser diode (LD), a phosphor, and the like, but is not limited thereto. The detector may include a photodiode, a photo transistor (PTr), and the like. However, the detector is not limited thereto, and may include a complementary metal-oxide semiconductor (CMOS) image sensor, a charge-coupled device (CCD) image sensor, and the like. The plurality of light sources may emit light of the same wavelength or light of different wavelengths. For example, the light sources may emit light of a green wavelength, a blue wavelength, a red wavelength, an infrared wavelength, etc., but the wavelength is not limited thereto. A plurality of detectors may be disposed at different distances from the light sources.

The sensor 110 may include a contact surface coming into contact with the object. The contact surface may be a smooth curved surface, but is not limited thereto.

The processor 120 may be electrically connected to the sensor 110. The processor 120 may control the sensor 110 in response to a user's request, and may receive a bio-signal from the sensor 110. The processor 120 may remove noise of contact pressure, caused by motion noise and the like, by performing preprocessing, such as filtering, smoothing, etc., on the received bio-signal.

In addition, the processor 120 may estimate a body component by using data received from the sensor 110. In this case, the body component may include triglyceride, blood glucose, electrolyte, carotenoid, body water, body fat, protein, alcohol, etc., but is not limited thereto.

For example, upon receiving a bio-signal from the sensor 110, the processor 120 may analyze the bio-signal to detect a time point at which an effect of local blood pressure is minimized. In addition, the processor 120 may detect a body component by using the time point at which the effect of local blood pressure is minimized.

Generally, local blood pressure of a body part may be changed due to a change in blood pressure of the central artery, a change in hydrostatic pressure, and the like, and a volume of blood vessels in the body part may be changed accordingly, thereby causing a change in a volume ratio between the internal body tissue and the blood vessels, and affecting a non-invasive bio-signal detection. Accordingly, by detecting a body component while minimizing the effect of local blood pressure, accuracy in detecting a body component may be improved. For example, the processor 120 may detect a time point at which an amplitude of an alternating current (AC) component of the bio-signal is maximum, or a time point at which a slope of a direct current (DC) component of the bio-signal is maximum, as the time point at which the effect of local blood pressure is minimized. However, the time point is not limited thereto.

The processor 120 may determine a time point, at which an amplitude of the AC component of the bio-signal is maximum, by using an amplitude graph of the AC component of the bio-signal with respect to contact pressure between the object and the sensor 110. In another example, the processor 120 may determine a time point, at which a slope of the DC component of the bio-signal is maximum, by using a slope graph of the DC component of the bio-signal with respect to the contact pressure between the object and the sensor 110.

Upon receiving a request for detecting a body component from, for example, a user, an external device, etc., the processor 120 may guide a user to place an object on the sensor 110, and once the object is in contact with the sensor 110, the processor 120 may guide the user to change contact pressure to be applied by the object to the sensor 110. For example, the processor 120 may guide the user to gradually increase a pressing force of the object being in contact with the sensor 110, or may guide the user to gradually decrease a pressing force when the user presses the sensor 110 with a force greater than or equal to a predetermined threshold. For example, by using a display module, an audio output module, and the like mounted in the apparatus 100 for detecting a body component or in an external device connected thereto, the processor 120 may provide guide information on the contact pressure for a user.

The processor 120 may extract a feature value from the bio-signal based on the determined time point, and may detect a body component based on the feature value.

The feature value may include any one or a combination of a contact pressure value at a time point, at which the amplitude of the AC component of the bio-signal is maximum, or a time point at which the slope of the DC component of the bio-signal is maximum, an amplitude value of the AC component, and a slope value of the DC component. However, the feature value is not limited thereto.

The processor 120 may estimate a body component by applying a pre-defined body component estimation model, as represented by the following Equation 1. The body component estimation model may be expressed in the form of various linear or non-linear combination functions, such as addition, subtraction, division, multiplication, logarithmic value, regression equation, and the like, with no specific limitation. For example, the following Equation 1 represents a simple linear function.

$$y=ax+b \quad \text{[Equation 1]}$$

Herein, y denotes a body component to be detected, for example, triglyceride, blood glucose, electrolyte, carotenoid, and the like; x denotes a feature value at a time point at which the effect of local blood pressure is minimized; and a and b are coefficients for weighting the feature value, and may be pre-defined fixed values universally applicable to a plurality of users according to the type of bio-information; or may be values adjusted for each user according to user characteristics and the like. In addition, the value x may be any one or a combination of two or more of the feature values. In this case, criteria for combining the feature values may be defined differently according to the type of body component to be obtained, and may be defined properly for each user according to user characteristics.

Figure 2:
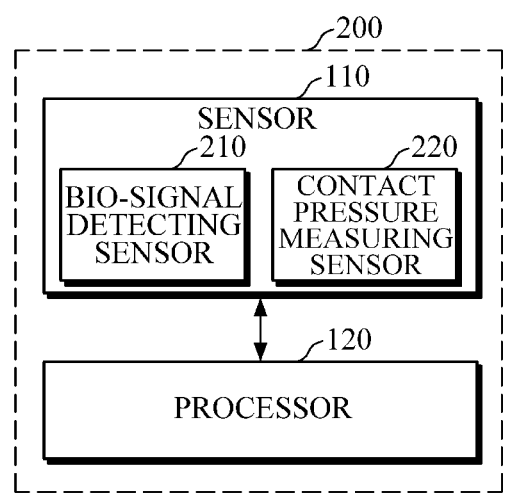
FIG. 2 is a block diagram illustrating an apparatus for detecting a body component according to another example embodiment.

FIG. 2 is a block diagram illustrating an apparatus for detecting a body component according to another example embodiment.

Referring to FIG. 2, an apparatus 200 for detecting a body component includes the sensor 110 and the processor 120.

As illustrated in FIG. 2, the sensor 110 may include a bio-signal detecting sensor 210 and a contact pressure measuring sensor 220.

The bio-signal detecting sensor 210 may include various sensors, such as a pulse wave sensor, an ultrasonic sensor, an impedance sensor, and the like, and may come into contact with the object to measure a bio-signal from the object.

The contact pressure measuring sensor 220 may measure contact pressure exerted between the object and the sensor 110 when the object, being in contact with the sensor 110, changes a force. The contact pressure measuring sensor 220 may include a pressure sensor, a combination of a force sensor and a contact area sensor, a pressure sensor array, etc., but is not limited thereto.

Once the contact pressure measuring sensor 220 of the sensor 110 measures the contact pressure, the processor 120 may generate guide information for guiding an actual force exerted by the object on the sensor 110. In this case, the guide information may include information for guiding the object to gradually increase pressure applied to the contact pressure measuring sensor 220 while the object is in contact with the contact pressure measuring sensor 220; or the guide information may include information for guiding the object to gradually decrease pressure when the object initially applies contact pressure greater than or equal to a predetermined threshold. Upon receiving the contact pressure of the object from the contact pressure measuring sensor 220, the processor 120 may request a user to re-measure the bio-signal if the received contact pressure falls outside a predetermined range, or may guide the user to apply contact pressure within the predetermined range.

Upon receiving the contact pressure of the object from the contact pressure measuring sensor 220, the processor 120 may generate an amplitude graph of the AC component of the bio-signal according to the received contact pressure, or a slope graph of the DC component of the bio-signal according to the received contact pressure. In this manner, the processor 120 may detect a time point, at which the amplitude of the AC component or the slope of the DC component is maximum, and may detect whether outlier data is generated due to motion noise. More details thereof will be provided later with reference to FIGS. 8A to 9B.

Figure 3:
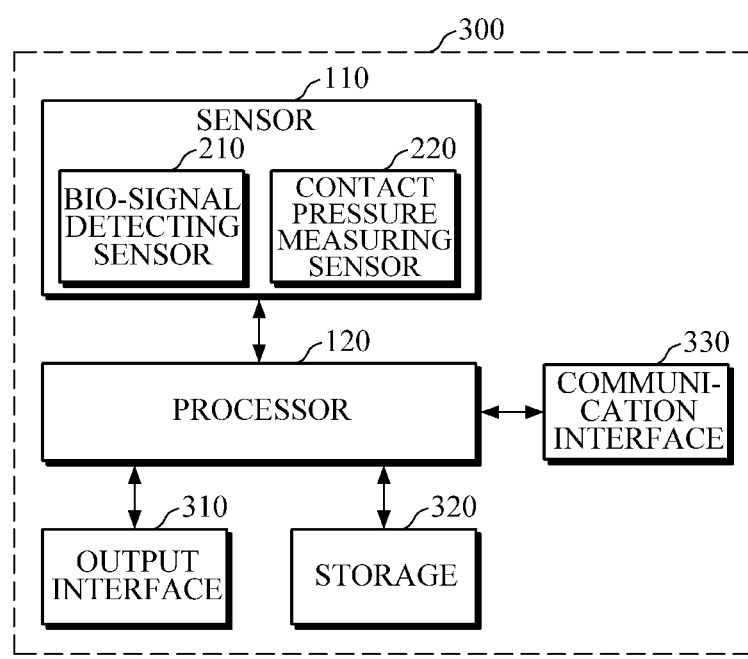
FIG. 3 is a block diagram illustrating an apparatus for detecting a body component according to yet another example embodiment.

FIG. 3 is a block diagram illustrating an apparatus for detecting a body component according to yet another example embodiment.

Referring to FIG. 3, an apparatus 300 for detecting a body component according to yet another embodiment includes an outputter (or an output interface) 310, a storage 320, and a communicator (or a communication interface) 330 in addition to the sensor 110 and the processor 120. The sensor 110 may include the bio-signal detecting sensor 210 and the contact pressure measuring sensor 220 as illustrated in FIG. 3, but is not limited thereto, and the contact pressure measuring sensor 220 may be omitted as illustrated in FIG. 1. The sensor 110 and the processor 120 are the same or similar to those described above, such that the following description will be focused on the outputter 310, the storage 320, and the communicator 330.

The outputter 310 may output the bio-signal obtained by the sensor 110, and an estimated body component value and/or guide information which are obtained by the processor 120. For example, the outputter 310 may visually output data, processed by the sensor 110 or the processor 120, through a display module, or may non-visually output the information by voice, vibrations, tactile sensation, and the like using a speaker module, a haptic module, and the like. In an example embodiment, a display area may be divided into two or more areas, in which the outputter 310 may output bio-signal values, contact pressure values, and the like in the form of various graphs in a first area; and along with the information, the outputter 310 may output a detected body component value in a second area. In an example embodiment, if the detected body component value falls outside a normal range, the outputter 310 may output warning information in various manners, such as highlighting an abnormal value in a certain color (e.g., red) and the like, displaying the abnormal value along with a normal range, outputting a voice warning message, adjusting a vibration intensity, and the like.

Further, the outputter 310 may output the guide information on the contact pressure, generated by the processor 120, and/or an actual contact pressure between a user's object and the sensor 110 which is measured by the contact pressure measuring sensor 220. For example, the outputter 310 may visually output the information through a display module, or may non-visually output the information by voice, vibrations, tactile sensation, and the like using a speaker module, a haptic module, and the like. For example, the outputter 310 may visually display, on the display, information on a predetermined range of contact pressure to be applied by a user for a measurement period of time and/or an actual contact pressure measured by the contact pressure measuring sensor 220.

The storage 320 may store processing results of the sensor 110 and/or the processor 120. Further, the storage 220 may store a variety of reference information to be used for estimating a body component. For example, the reference information may include user characteristic information such as a user's age, sex, health condition, and the like. In addition, the reference information may include information such as a body component estimation model, criteria for estimating a body component, a reference contact pressure set for each user, and the like, but is not limited thereto.

In this case, the storage 320 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communicator 330 may communicate with an external device by using wired or wireless communication techniques under the control of the processor 120, and may transmit and receive various data to and from the external device. For example, the communicator 330 may transmit a body component detection result to the external device, and may receive, from the external device, a variety of reference information used for detecting a body component. The external device may include a cuff-type blood pressure measuring device and an information processing device such as a smartphone, a tablet PC, a desktop computer, a laptop computer, and the like.

Examples of the communication techniques used by the communicator 330 may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, these are only examples and are not intended to be limiting.

Figure 4A:
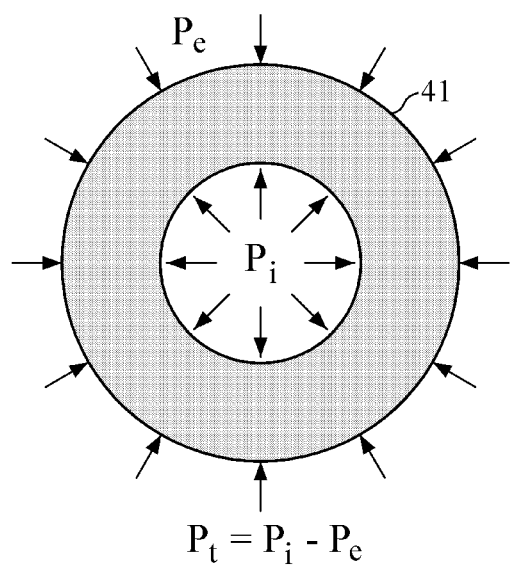
FIGS. 4A, 4B and 4C are diagrams illustrating vascular volume and compliance according to a difference in pressure applied to a wall of blood vessels.
Figure 4B:
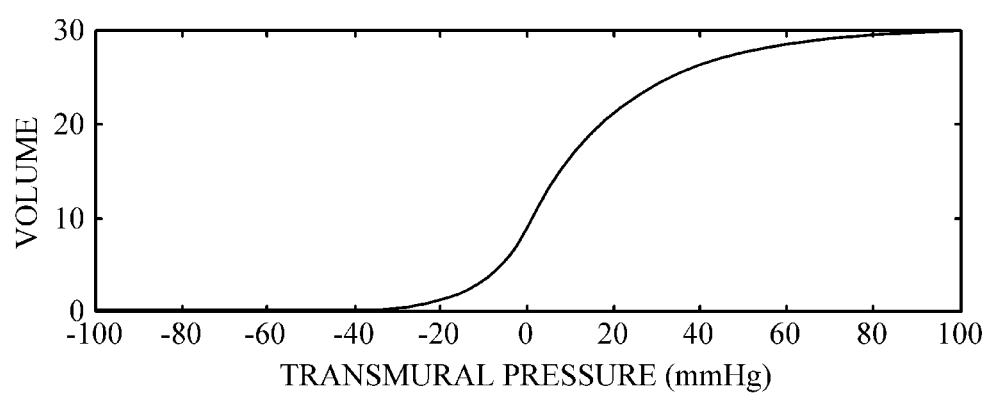
Figure 4C:
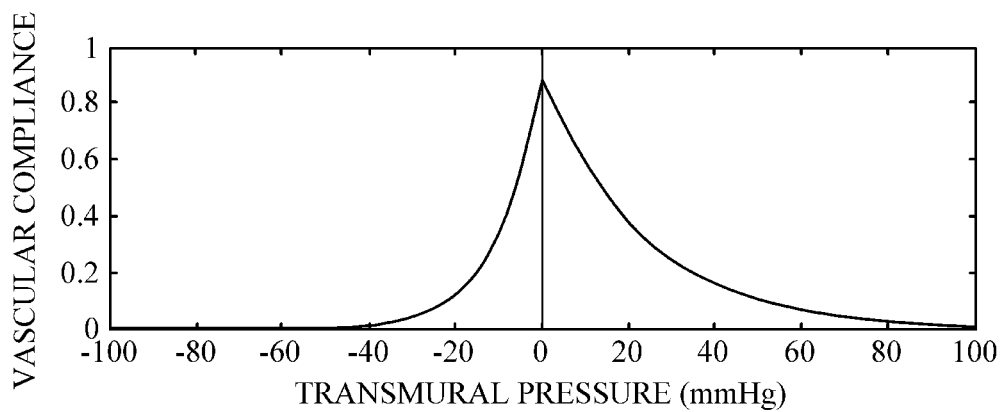

FIGS. 4A, 4B, and 4C are diagrams illustrating vascular volume and compliance according to a difference in pressure applied to a wall of blood vessels.

Referring to FIG. 4A, transmural pressure Pt may be defined as a value obtained by subtracting external pressure Pe from internal pressure Pi exerted on a blood vessel 41. Here, the external pressure Pe may refer to contact pressure exerted by the object on the sensor 110 as the object changes a pressing force on the sensor 11, and the internal pressure Pi may refer to blood pressure.

Referring to a graph of FIG. 4B, the horizontal axis indicates the transmural pressure Pt, i.e., a difference between the external pressure and blood pressure, and the vertical axis indicates a vascular volume. It can be seen from FIG. 4B that as the transmural pressure Pt increases, the blood vessel volume increases non-linearly.

Referring to a graph of FIG. 4C, the horizontal axis indicates the transmural pressure Pt, i.e., a difference between the external pressure and blood pressure, and the vertical axis indicates vascular compliance. It can be seen from FIG. 4C that as the transmural pressure Pt increases, the vascular compliance increases, but at a time when the blood pressure is equal to the external pressure, i.e., at a time when the transmural pressure is zero, the vascular compliance is maximum and then decreases thereafter as the transmural pressure Pt increases. In other words, at the time when the blood pressure is equal to the external pressure, the vascular compliance is maximum.

Figure 5A:
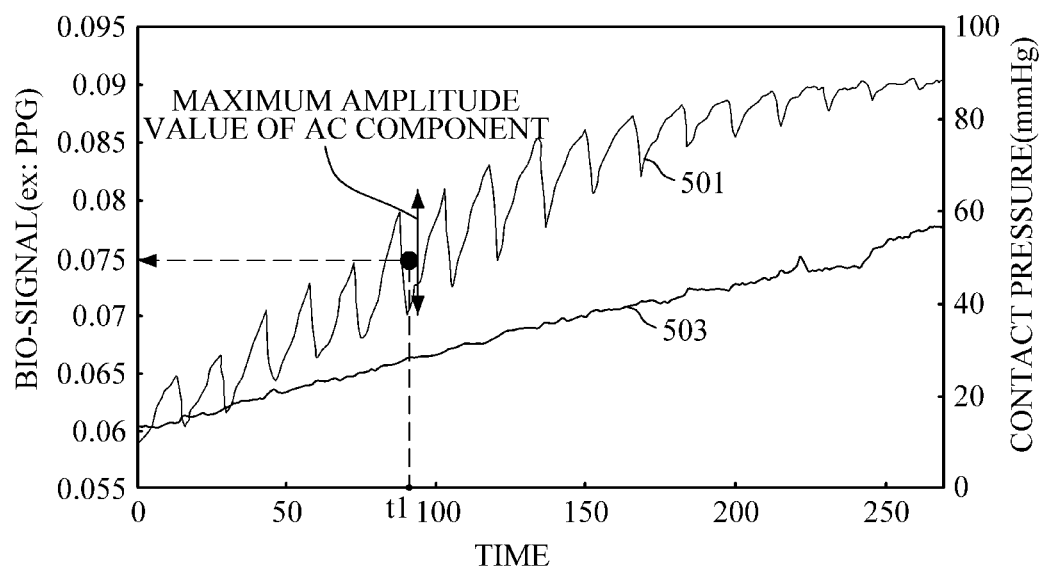
FIGS. 5A and 5B are diagrams for explaining a time point at which an effect of local blood pressure is minimized.
Figure 5B:
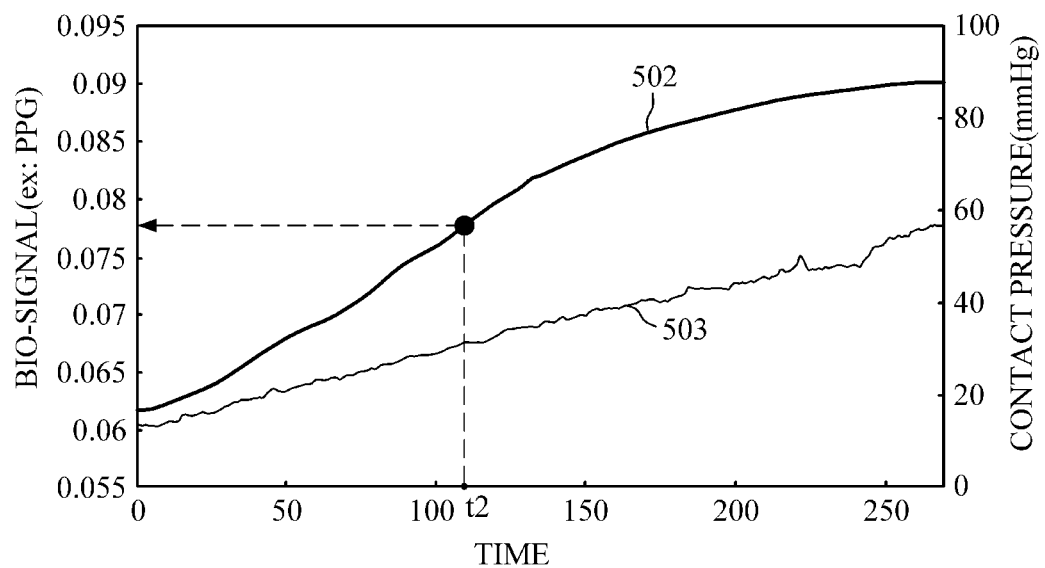

FIGS. 5A and 5B are diagrams for explaining a time point at which an effect of local blood pressure is minimized.

FIG. 5A is a graph showing an AC component 501 of a bio-signal according to a lapse of time, in which the horizontal axis indicates the time, the left vertical axis indicates the bio-signal, and the right vertical axis indicates the contact pressure.

When a user gradually increases a pressing force of the object on the sensor 110, contact pressure 503 between the object and the sensor 110 gradually increases as illustrated in FIG. 5A. In this case, an amplitude of the AC component 501, measured by the sensor 110, first increases and then decreases when the contact pressure increases to a predetermined pressure or more. This is due to non-linear characteristics of the vascular compliance as shown in FIGS. 4A and 4B. That is, as the contact pressure gradually increases, the external pressure gradually increases such that at a time point t1, the transmural pressure, i.e., a difference between the external pressure and the internal pressure, becomes zero; and at this time point, a cross-sectional area of the blood vessel has a value irrelevant to the local blood pressure of the object being in contact with the sensor 110.

Referring to the illustrated example, the processor 120 may detect a time point at which the transmural pressure is zero, i.e., a time when a volume increasing rate and the vascular compliance are maximum, and the processor 120 may detect the time point t1 as a time point at which the effect of local blood pressure is minimized.

FIG. 5B is a graph showing the DC component of the bio-signal according to a lapse of time, in which the horizontal axis indicates the time, the left vertical axis indicates the bio-signal, and the right vertical axis indicates the contact pressure.

The processor 120 may obtain a DC component signal, from which pulsation is eliminated by filtering the bio-signal. In this case, the processor 120 may perform filtering by using a low pass filter, but is not limited thereto. Generally, capillaries and veins in a body part have low pulsation but occupy a large volume, thereby mainly affecting the DC component of the bio-signal. Accordingly, if it is important to maintain a cross-sectional area of the capillaries and the veins at a constant value, the processor 120 may detect a time point, at which the effect of local blood pressure on the bio-signal is minimum, by using a slope value of the DC component of the bio-signal.

Referring to FIG. 5B, contact pressure increases according to a lapse of time, similar to FIG. 5A. The time point, at which the transmural pressure is zero, may be a time point t2 at which a slope of the DC component is maximum, and the processor 120 may detect the time point t2 as a time point at which the effect of local blood pressure is minimized.

As described above, by detecting the time point at which the effect of local blood pressure is minimized, and by estimating a body component based on the time point, accuracy in the estimated body component value may be improved. For example, in comparison of a blood pressure level of 100 with a blood pressure level of 120, contact pressure between the object and the sensor is higher at the blood pressure level of 120 than the blood pressure level of 100, resulting in a higher degree of pressing of the object. In this case, a gap between internal tissues of the object decreases by the contact pressure in the case of the pressure level of 120 compared to the blood pressure level of 100, thereby having different effects on body component values. Accordingly, by detecting a body component at the time point at which the effect of local blood pressure is minimized, the accuracy in detecting a body component may be improved.

Figure 6A:
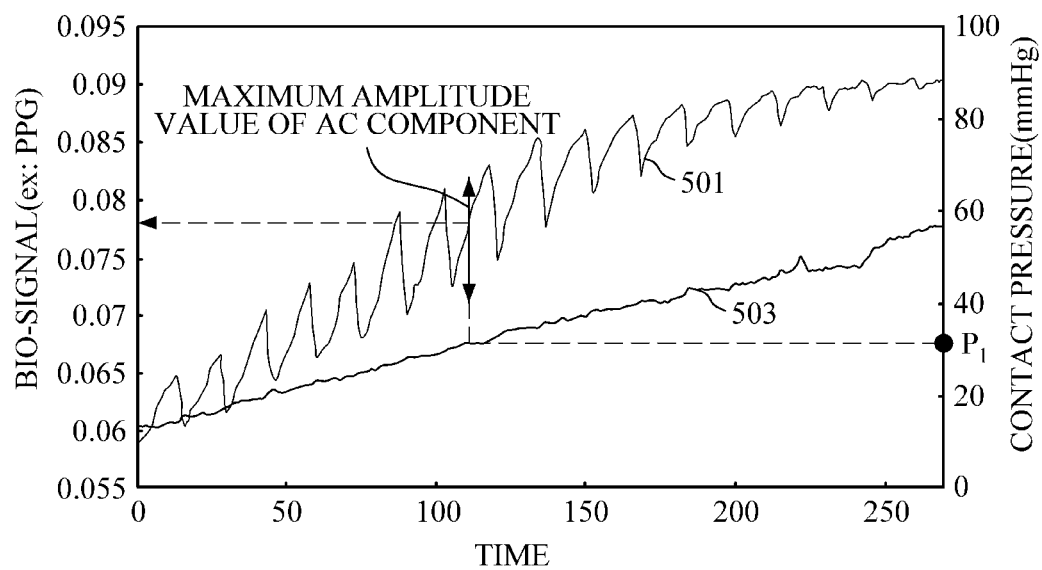
FIGS. 6A and 6B are diagrams illustrating graphs of contact pressure versus amplitude of an alternating current (AC) component.
Figure 6B:
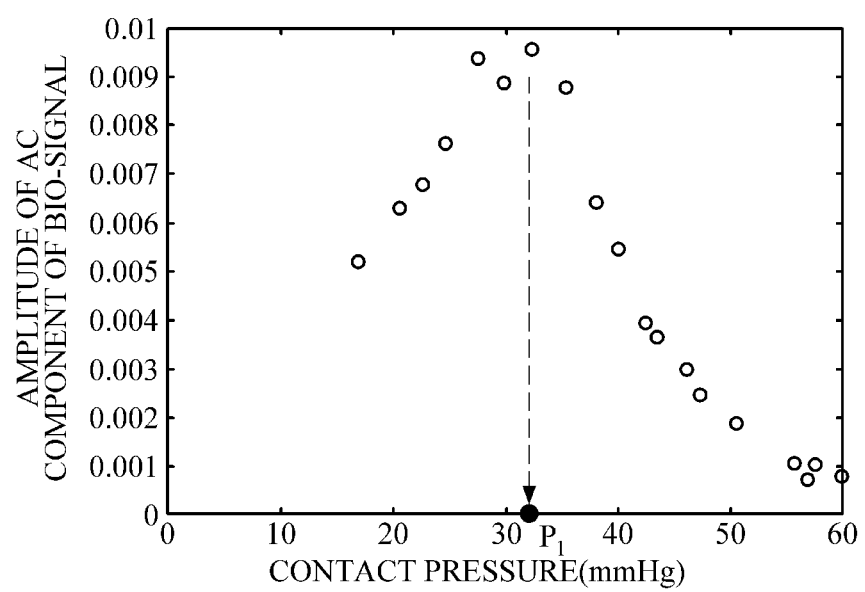

FIGS. 6A and 6B are diagrams illustrating graphs of contact pressure versus amplitude of an AC component.

Referring to FIG. 6A, contact pressure 503 gradually increases with time. In this case, it can be seen that an amplitude of an AC component 501 of the bio-signal gradually increases to be maximum at a time point at which contact pressure is P1, and then decreases thereafter. The processor 120 may generate a graph by plotting amplitude values at each measurement time against contact pressure values at a corresponding time. The generated graph is illustrated in FIG. 6B.

It can be seen based on FIGS. 6A and 6B whether the contact pressure increases consistently with measurement time, whether outlier data is generated due to motion noise, and the like. As will be described below, the processor 120 may remove outlier data or may determine a maximum point of the AC component based on the graph of the contact pressure versus amplitude of the AC component.

Figure 7A:
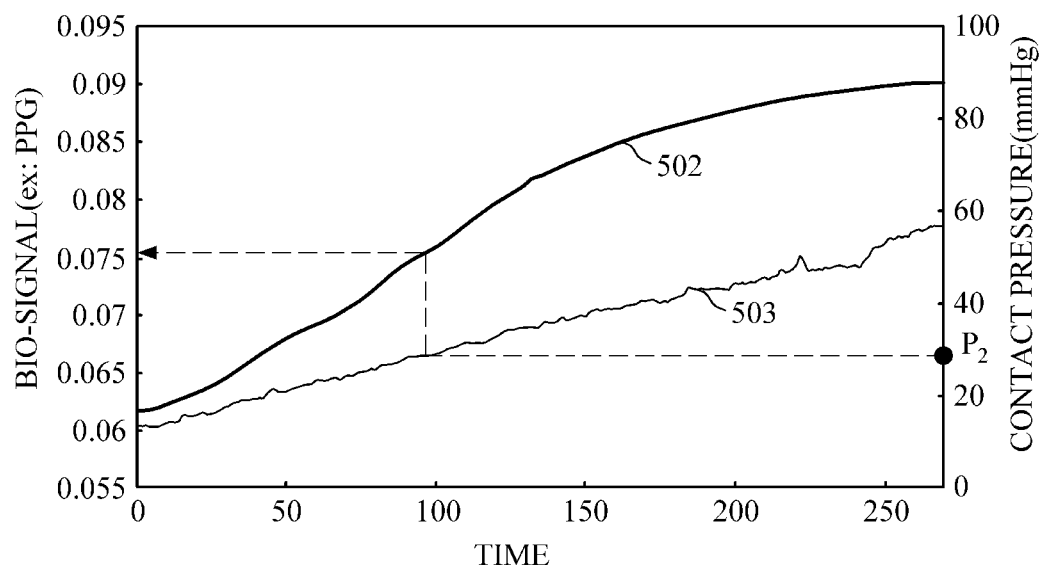
FIGS. 7A and 7B are diagrams illustrating graphs of contact pressure versus slope of a direct current (DC) component.
Figure 7B:
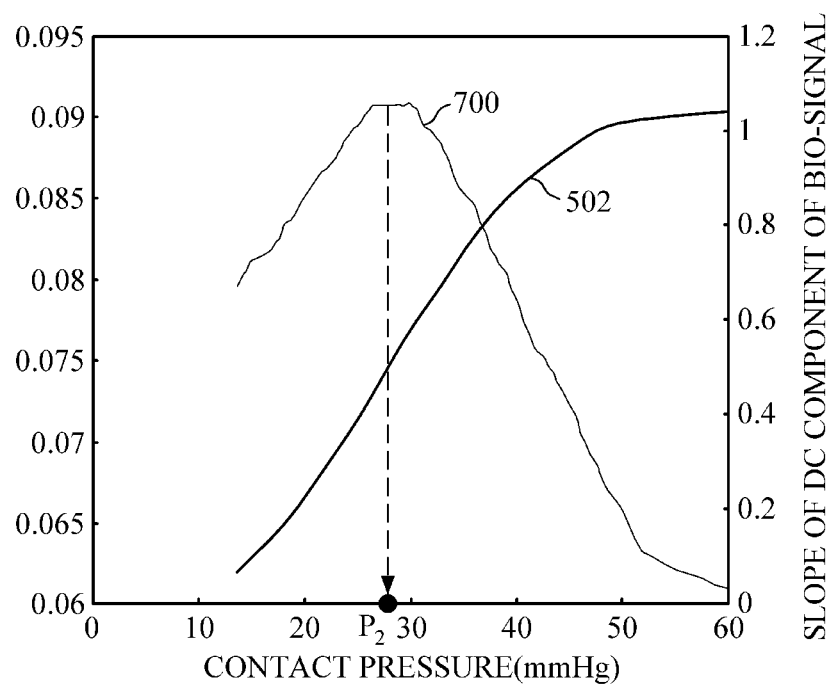

FIGS. 7A and 7B are diagrams illustrating graphs of contact pressure versus slope of a DC component.

FIG. 7A illustrates a relationship between the contact pressure 503 and a DC component 502 of the bio-signal according to a lapse of time. As illustrated in FIG. 7A, as the contact pressure 503 gradually increases, the DC component 502 of the bio-signal also increases. FIG. 7A illustrates an example in which as the contact pressure 503 increases, a slope of the DC component 502 gradually increases to be maximum at a time point at which the contact pressure is P2, and then decreases thereafter.

FIG. 7B illustrates a graph generated by plotting the DC component 502 against the contact pressure 503 of FIG. 7A. The graph shows the DC component 502 according to an increase in contact pressure, and a slope 700 obtained by differentiating the DC component 502. Referring to FIG. 7B, a change in slope of the DC component of the bio-signal at each contact pressure may be easily identified, such that a time point at which a slope value of the DC component of the bio-signal is maximum may be detected. Further, noise due to an erroneous operation by a user may be determined based on the graph; and based on the determination, it is possible to request the user to re-measure the bio-signal or to correct a slope value of the DC component. Details of correcting the slope value or determining noise will be provided below.

Figure 8A:
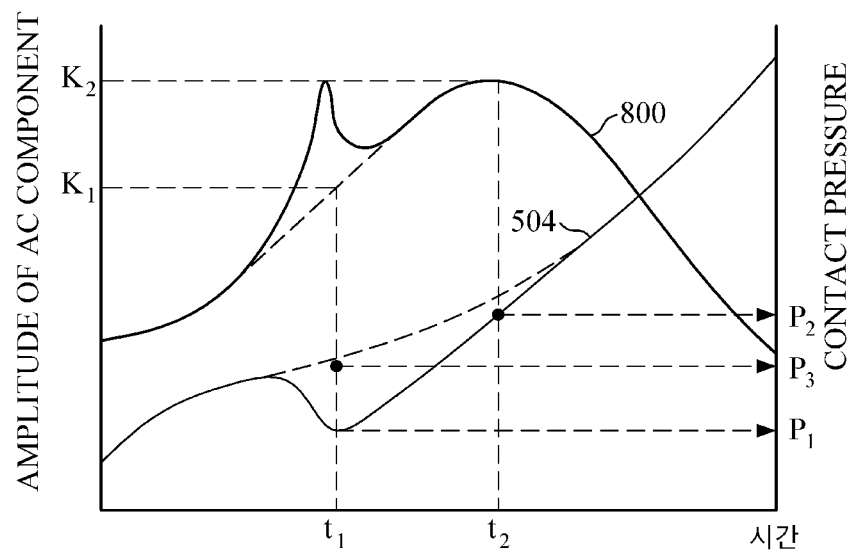
FIGS. 8A and 8B are diagrams for explaining an example of removing outlier data from a bio-signal and correcting the bio-signal.
Figure 8B:
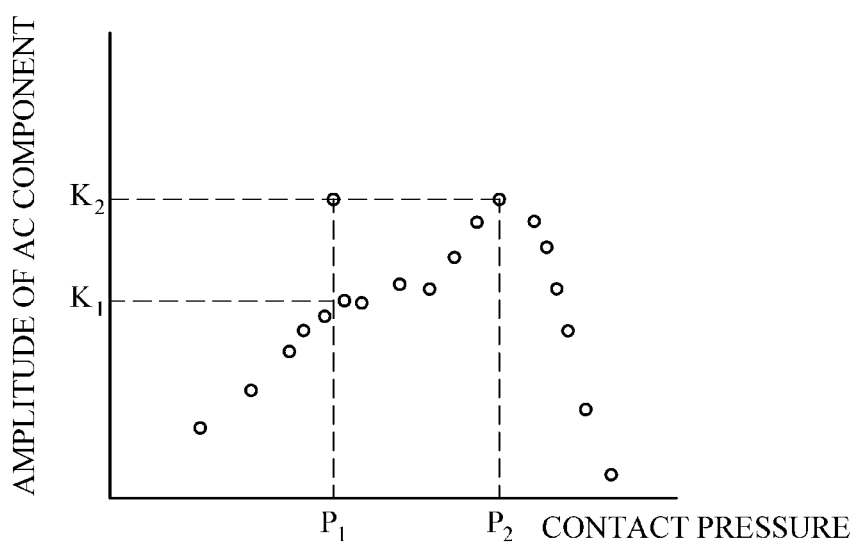

FIGS. 8A and 8B are diagrams for explaining an example of removing outlier data from a bio-signal and correcting the bio-signal. FIGS. 8A and 8B illustrate the outlier data of amplitude values of the AC component of the bio-signal, but the description may also apply to slope values of the DC component of the bio-signal.

FIG. 8A illustrates an example in which an amplitude of the AC component increases significantly due to motion noise occurring at a predetermined time. While FIG. 6A illustrates an example in which contact pressure gradually increases during measurement of the bio-signal, FIG. 8A illustrates an example in which contact pressure 504 suddenly decreases to a low value at a time t1 due to motion noise. As illustrated in FIG. 8A, in the case where motion noise occurs at the time t1 such that contact pressure is abnormally applied, an amplitude 800 of the AC component at the time t1 may increase significantly. That is, if motion noise does not occur at the time t1, the measured amplitude value of the AC component is K1, but contact pressure suddenly decreases to a pressure value of P1 due to an erroneous operation by a user, such that the measured value of the AC component of the bio-signal increases to K2.

FIG. 8B illustrates a graph representing a relationship between the contact pressure and the amplitude of the AC component shown in the graph of FIG. 8A. In FIG. 8B, the horizontal axis indicates the contact pressure, and the vertical axis indicates the amplitude of the AC component. Referring to FIG. 8B, as the contact pressure increases, an amplitude value of the AC component first increases and then decreases after a point of a predetermined contact pressure (P2). It can be seen from FIG. 8B that at a point where the contact pressure is P1, the amplitude of the AC component deviates from a trend of a change in increase and decrease in the graph. That is, referring to FIG. 8B, the contact pressure P1 is measured at the time t1, which is lower than the contact pressure P2 at the time t2, at which a maximum amplitude value of the AC component of the bio-signal is normally detected. However, the AC component of the bio-signal at the time t1 has the amplitude value K2, which is equal to the amplitude value K2 of the AC component at the time t2. As described above, if an amplitude value corresponding to the maximum amplitude value is detected at the time t1, other than the time t2 at which the maximum amplitude value of the AC component of the bio-signal is normally detected, or if the contact pressure P1 falling outside a predetermined threshold is applied compared to the contact pressure P3 to be normally applied at the time t1, the processor 120 may detect an amplitude value at the time t1 as outlier data.

For example, in order to remove outlier data from the amplitude value of the AC component or the slope value of the DC component of the bio-signal, the processor 120 may perform filtering on the amplitude graph of the AC component or the slope graph of the DC component of the bio-signal. In this case, the processor 120 may perform filtering by using a noise filter for attenuating a noise component and passing a corresponding signal component, but the filtering is not limited thereto.

In another example, the processor 120 may generate a connected graph by connecting each data in the amplitude graph of the AC component of the bio-signal according to the contact pressure as illustrated in FIG. 8B, and may perform differentiation on the generated graph. In this case, the outlier data in the connected graph may be a discontinuous point, which may not be differentiated such that no differentiated value is obtained at the time point at which the outlier data is generated. The processor 120 may detect an amplitude value at a time point, at which no differentiated value is obtained in the differentiation graph, as the outlier data and may remove the outlier data.

In addition, upon detecting the outlier data, the processor 120 may guide a user to re-measure the bio-signal, or may control the sensor 110 to re-measure the bio-signal. In this case, if a number of the detected outlier data is greater than or equal to a predetermined number, the processor 120 may guide the user to re-measure the bio-signal, or otherwise may remove the outlier data as described above.

In yet another example, if the amplitude of the AC component or the slope of the DC component in the bio-signal is greater than or equal to a predetermined threshold at a plurality of time points, the processor 120 may correct the amplitude value of the AC component or the slope value of the DC component of the bio-signal. For example, the processor 120 may calculate a moving average of the amplitude value of the AC component or the slope value of the DC component in units of predetermined intervals. In this case, the predetermined intervals may be set according to the computing performance of a device, the type of component to be analyzed, and the like. The processor 120 may determine a maximum amplitude value or a maximum slope value by using the corrected amplitude of the AC component or the corrected slope of the DC component.

Figure 9A:
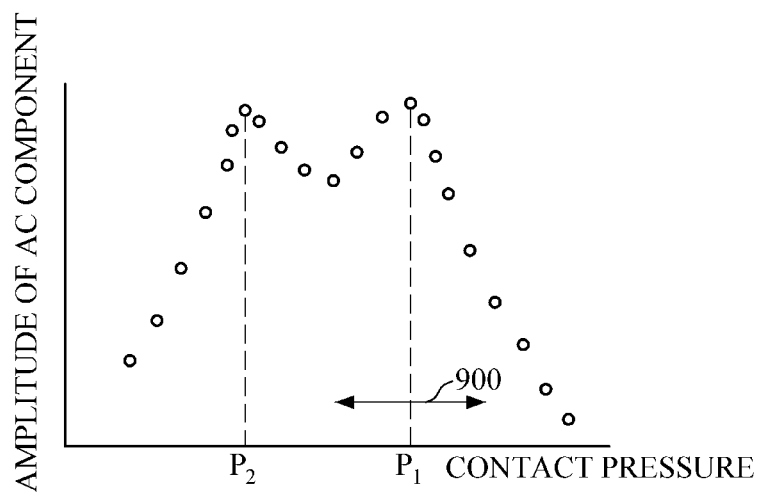
FIGS. 9A and 9B are diagrams for explaining a method of determining a time point, at which an effect of local blood pressure is minimized, within a reference contact pressure range.
Figure 9B:
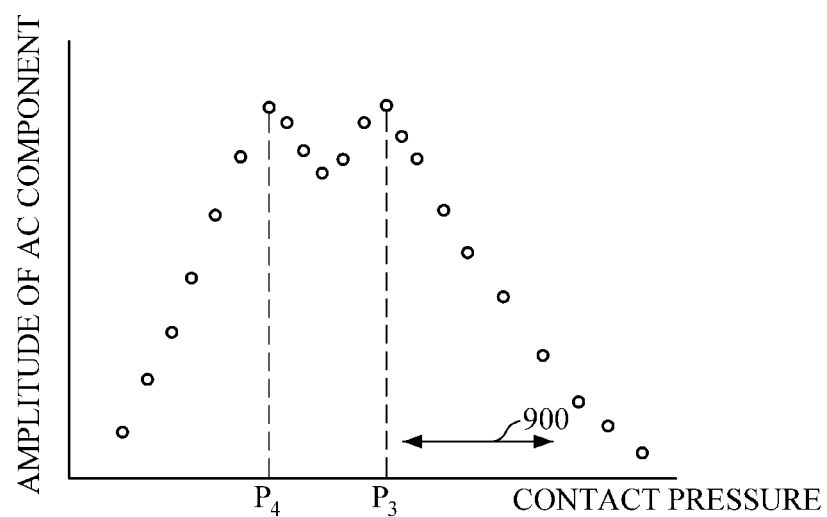

FIGS. 9A and 9B are diagrams for explaining a method of determining a time point, at which an effect of local blood pressure is minimized, within a reference contact pressure range.

The processor 120 may determine a time point, at which an amplitude of the AC component is maximum or a slope of the DC component is maximum, within a reference contact pressure range 900, which is set for each user based on the measured contact pressure, to be a time point at which the effect of local blood pressure is minimized. The time point, at which the effect of local blood pressure is minimized, may vary for each user according to finger elasticity and a measurement method. However, if no motion noise occurs, a time point at which the effect of local blood pressure is minimized, may be detected for a specific user within a predetermined contact pressure range. Accordingly, by performing calibration at a time when a specific user is in a resting state, the processor 120 may detect a point where the amplitude of the AC component or the slope of the DC component is maximum for the user, and may set a reference contact pressure range for the user based on the detected point. However, the reference contact pressure range is not limited thereto, and for example, may be set based on a previous estimating history of the specific user.

Upon obtaining the bio-signal from the specific user, the processor 120 may detect a point, at which the effect of local blood pressure is minimized, within the reference contact pressure range set for the user, and may rapidly detect the point regardless of whether motion noise occurs in other range.

Referring to FIG. 9A, it can be seen that there are a plurality of time points at which the amplitude value of the AC component is maximum, but the contact pressure P1 at one time point is within the reference contact pressure range 900 set for each user, and the contact pressure P2 at another time point is outside the reference contact pressure range 900 set for each user. Of the two time points, the processor 120 may determine a time point, at which the contact pressure P1 is measured within the reference contact pressure range 900 set for each user, to be the time point at which the effect of local blood pressure is minimized.

Referring to FIG. 9B, it can be seen that there are a plurality of time points at which the amplitude value of the AC component is maximum, but both the contact pressure values P3 and P4 at the respective time points are outside the reference contact pressure range 900 set for each user. The processor 120 may request the user to re-measure the bio-signal without determining the two time points to be the time point at which the effect of local blood pressure is minimized.

Figure 10:
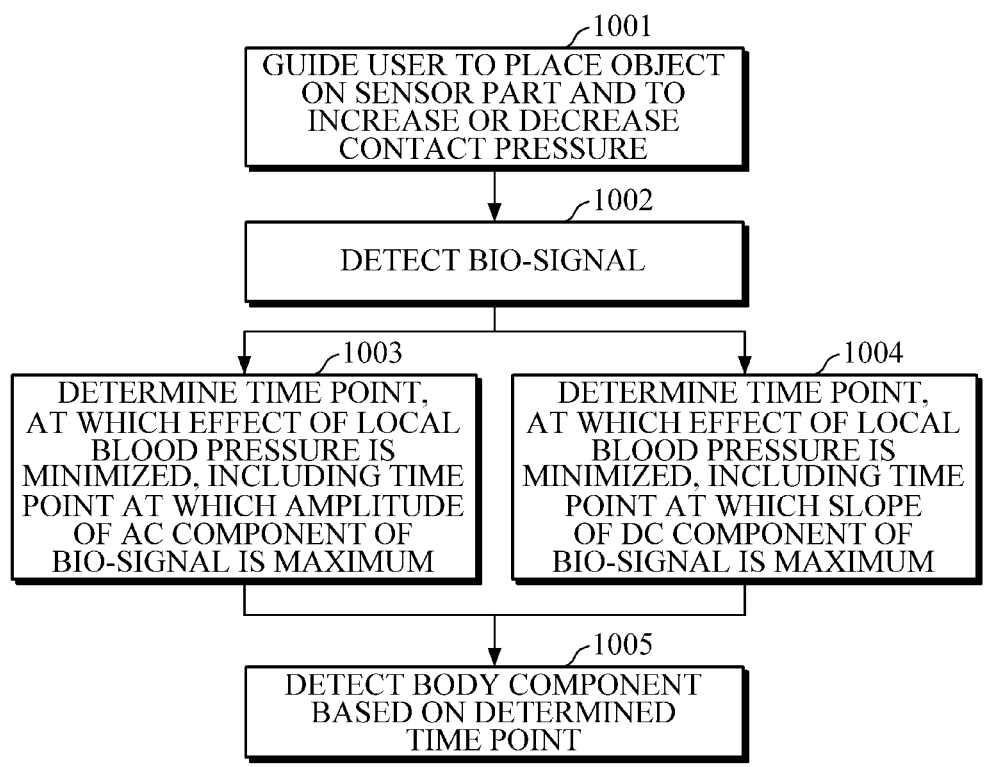
FIG. 10 is a flowchart illustrating a method of detecting a body component according to an example embodiment.

FIG. 10 is a flowchart illustrating a method of detecting a body component according to an example embodiment.

The method of FIG. 10 is an example of a method of detecting a body component which may be performed by any one of the apparatuses 100, 200, and 300 for detecting a body component, which is described above in detail and thus will be briefly described below.

First, the apparatus for detecting a body component may guide a user to place an object on the sensor and to increase or decrease contact pressure in 1001.

Then, the apparatus for detecting a body component may detect a bio-signal from the object in 1002 when the object, being in contact with the sensor, changes contact pressure according to the guide.

Subsequently, the apparatus for detecting a body component may determine a time point, at which an effect of local blood pressure is minimized, including a time point at which an amplitude of an AC component in 1003 or a slope of a DC component is maximum in the bio-signal in 1004. In this case, the apparatus for detecting a body component may further perform filtering on the AC component or the DC component of the bio-signal, to remove outlier data. Alternatively, by differentiating the filtered bio-signal and then detecting a point having an amplitude value or a slope value, which is greater than a first predetermined threshold value, or which is less than or equal to a second predetermined threshold value, from the differentiated bio-signal, the apparatus for detecting a body component may remove an amplitude value at the detected point. Further, by calculating a moving average of the amplitude value of the AC component or the slope value of the DC component of the measured bio-signal in units of predetermined intervals, the apparatus for detecting a body component may correct the amplitude or slope values.

Next, the apparatus for detecting a body component may detect a body component based on the determined time point in 1005.

Figure 11:
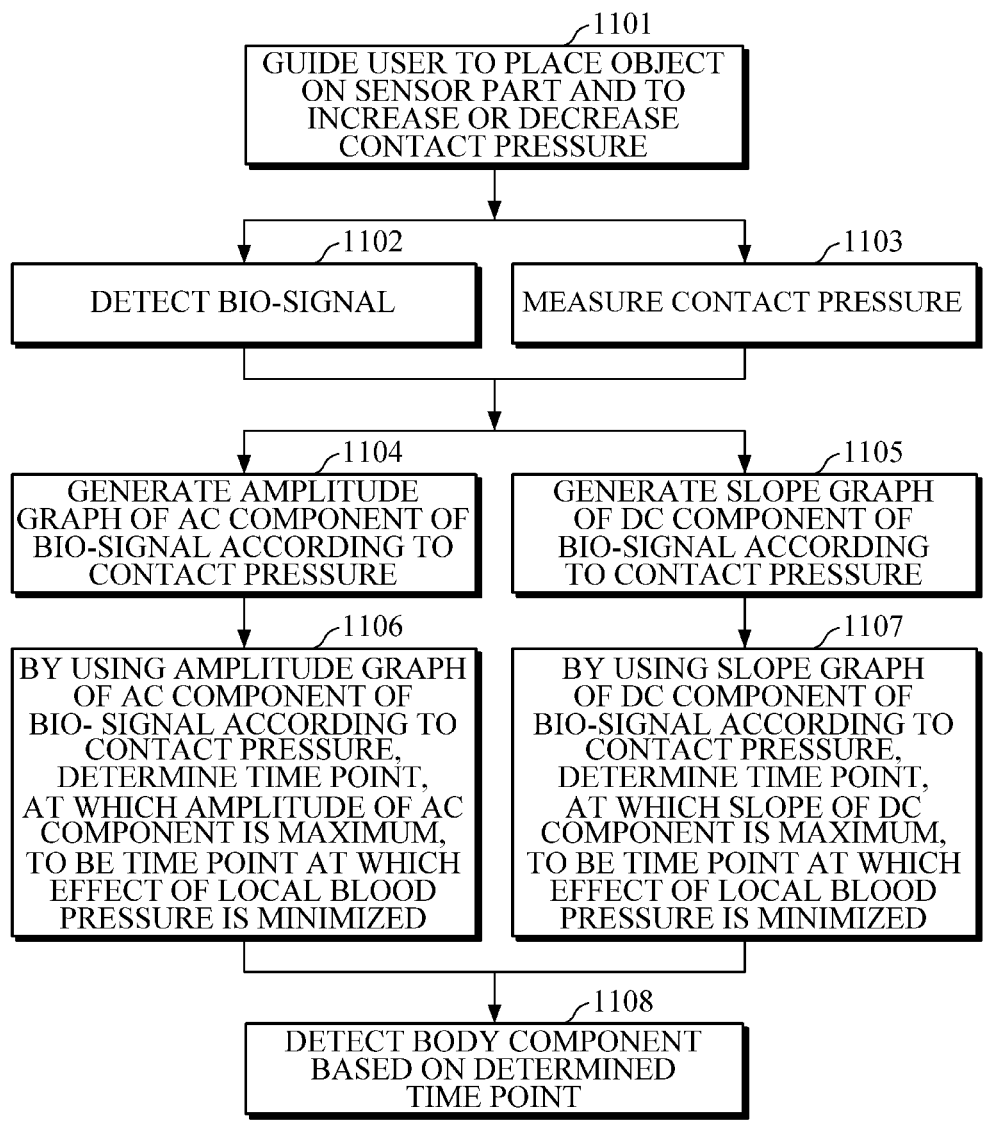
FIG. 11 is a flowchart illustrating a method of detecting a body component according to another example embodiment.

FIG. 11 is a flowchart illustrating a method of detecting a body component according to another example embodiment.

The method of FIG. 11 is an example of a method of detecting a body component which may be performed by any one of the apparatuses 100, 200, and 300 for detecting a body component, which is described above in detail and thus will be briefly described below.

First, the apparatus for detecting a body component may guide a user to place an object on the sensor and to increase or decrease contact pressure in 1101.

Then, the apparatus for detecting a body component may detect a bio-signal from the object in 1102 when the object, being in contact with the sensor, changes contact pressure according to the guide.

Subsequently, the apparatus for detecting a body component may measure contact pressure when the object, being in contact with the sensor, changes a pressing force on the sensor in 1103. In this case, the apparatus for detecting a body component may guide a user on the contact pressure based on the measured contact pressure.

Next, the apparatus for detecting a body component may generate an amplitude graph of the AC component of the bio-signal according to contact pressure in 1104, or may generate a slope graph of the DC component of the bio-signal according to contact pressure in 1105.

Then, by using the amplitude graph of the AC component of the bio-signal according to contact pressure, the apparatus for detecting a body component may detect a time point at which the amplitude of the AC component of the bio-signal is maximum in 1106; or by using the slope graph of the DC component of the bio-signal according to contact pressure, the apparatus for detecting a body component may detect a time point at which the slope of the DC component is maximum in 1107. Upon obtaining contact pressure at a point having a highest resulting value in the amplitude graph of the AC component or the slope graph of the DC component of the bio-signal according to the contact pressure, and then by detecting a time point at which the corresponding contact pressure is applied, the apparatus for detecting a body component may detect a time point at which the effect of local blood pressure is minimized.

Subsequently, the apparatus for detecting a body component may detect a body component based on the determined time point in 1108.

Figure 12:
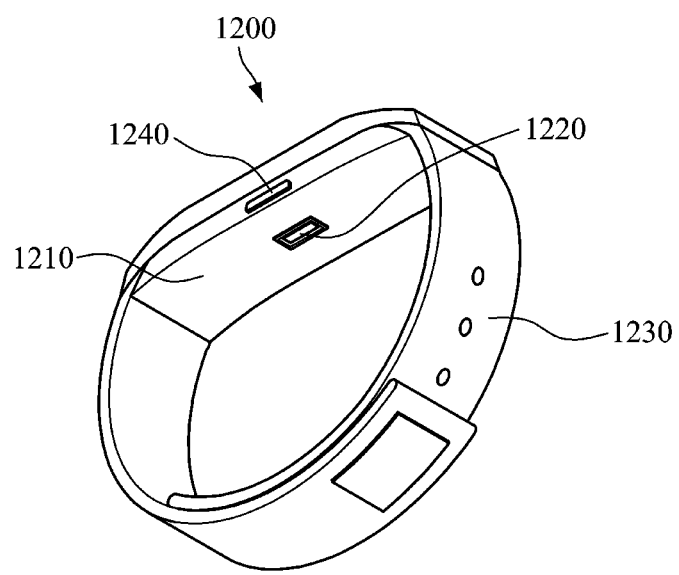
FIG. 12 is a diagram illustrating a wearable device according to an example embodiment.

FIG. 12 is a diagram illustrating a wearable device according to an example embodiment.

Referring to FIG. 12, the wearable device 1200 includes a main body 1210 and a strap 1230.

The strap 1230, which is connected to both ends of the main body 1210, may be flexible so as to be wrapped around a user's wrist. The strap 1230 may include a first strap and a second strap which are separated from each other. One ends of the first strap and the second strap are connected to the main body 1210, and the other ends thereof may be connected to each other via a connecting means. In this case, the connecting means may be formed as magnetic connection, Velcro connection, pin connection, and the like, but is not limited thereto. Further, the strap 1230 is not limited thereto, and may be integrally formed as a non-detachable band. In this case, air may be injected into the strap 1230, or the strap 1230 may be provided with an air bladder to have elasticity according to a change in pressure applied to the wrist, and may transmit the change in pressure of the wrist to the main body 1210.

A battery may be embedded in the main body 1210 or the strap 1230 to supply power to the wearable device 1200.

The main body 1210 may include a sensor 1220 mounted on one side thereof. The sensor 1220 may include a sensor for detecting a bio-signal and a sensor for measuring contact pressure. The bio-signal detecting sensor may include a light source and a CMOS Image Sensor (CIS). In addition, the contact pressure measuring sensor r ay include a force sensor, a pressure sensor, an area sensor, and the like.

A processor may be mounted in the main body 1210. The processor may determine a time point, at which the effect of local blood pressure is minimized, in the bio-signal detected by the sensor. For example, the processor may determine a time point, at which the amplitude of the AC component or the slope of the DC component is maximum, to be the time point at which the effect of local blood pressure is minimized. In addition, the processor may extract a feature value based on the determined time point, and may detect a body component based on the extracted feature value.

Upon receiving a request from detecting a body component from a user, the processor may provide guide information on force/pressure for the user; and upon estimating a body component, the processor may provide the estimation result for the user through a display. The display may be mounted on a front surface of the main body 1210. The display may output the guide information and/or the body component estimation result, and may receive a user's touch input and transmit the touch input to the processor.

Furthermore, the main body 1210 may include a storage which stores information processed by the processor and reference information for detecting a body component, and the like.

In addition, the main body 1210 may include a manipulator 1240 which receives a user's control command and transmits the received control command to the processor. The manipulator 740 may be provided on one side surface of the main body 1210, and may have a power button to input a command to turn on/off the wearable device 1200.

Moreover, the wearable device 1200 may include a communicator (or a communication interface) for transmitting and receiving various data with an external device, and various other modules for additional functions provided by the wearable device 1200.

Figure 13:
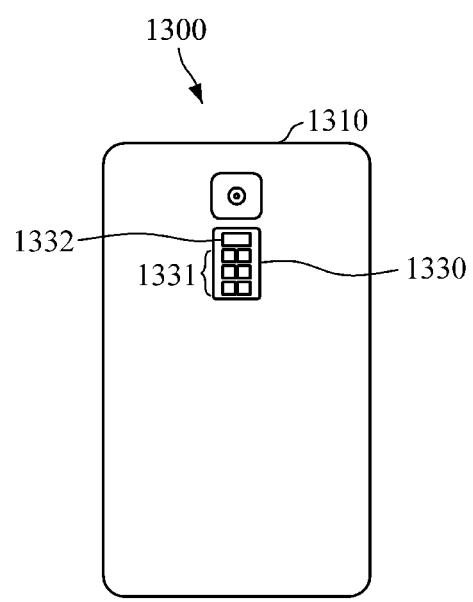
FIG. 13 is a diagram illustrating a smart device according to an example embodiment.

FIG. 13 is a diagram illustrating a smart device according to an example embodiment.

FIG. 13 illustrates a smart device, to which the embodiments of the apparatus for estimating bio-information are applied. The smart device may include a smartphone, a tablet PC, and the like.

Referring to FIG. 13, the smart device 1300 includes a main body 1310 and a sensor 1330 mounted on one surface of the main body 1310. The sensor 1330 may include one or more light sources 1331 and a detector 1332, and may detect bio-information.

Further, the sensor 1330 may include a sensor for measuring contact pressure between the object and the sensor. In this case, the detector 1332 may include a CMOS image Sensor (CIS).

A processor may be mounted in the main body 1310, and may estimate a body component, such as triglyceride, blood glucose, electrolyte, carotenoid, and the like based on the bio-signal and contact pressure estimated by the sensor 1330.

In addition, a display, a communicator, and the like may be mounted in the main body 1310, and may output and provide bio-information processed by the processor 1310 for a user or may transmit the bio-information to other external devices. Furthermore, various modules for performing various functions of the main body 1310 may be mounted therein.

The disclosure may be implemented as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium may be distributed over a plurality of computer systems connected to a network so that a computer-readable code is written thereto and executed therefrom in a decentralized manner. Functional programs, codes, and code segments for implementing the disclosure may be readily deduced by programmers of ordinary skill in the art to which the disclosure pertains.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like.

While the disclosure has been particularly shown and described with reference to example embodiments thereof, it will be understood that various changes in form and details may be made therein without departing from the spirit and scope of the following claims.

What is claimed is:

1. An apparatus for non-invasively detecting a body component, while minimizing an effect of local blood pressure, the apparatus comprising:
   a sensor configured to detect a bio-signal of an object according to a contact pressure that gradually changes between the object and the sensor; and
   a processor configured to determine a time point, at which an amplitude of an alternating current (AC) component of the bio-signal is maximum or a slope of a direct current (DC) component of the bio-signal is maximum, and to detect a body component of the object based on the determined time point,
   wherein the processor is further configured to perform filtering on the bio-signal to remove noise in the contact pressure, and differentiate the filtered bio-signal, and
   wherein the processor is further configured to detect a point having a value greater than a first predetermined threshold value, or a point having a value equal to or less than a second predetermined threshold, from the differentiated bio-signal, and prior to determining the time point, remove an amplitude value of the filtered bio-signal at the detected point.

2. The apparatus of claim 1, wherein the processor is further configured to perform filtering on the amplitude of the AC component or the slope of the DC component, to remove outlier data.

3. The apparatus of claim 1, wherein based on a detection of a plurality of time points, at which the amplitude of the AC component or the slope of the DC component in the bio-signal is greater than or equal to a predetermined threshold, the processor is further configured to correct the amplitude of the AC component or the slope of the DC component.

4. The apparatus of claim 3, wherein the processor is further configured to correct an amplitude value of the AC component or a slope value of the DC component by obtaining a moving average of the amplitude value of the AC component or the slope value of the DC component in units of predetermined intervals.

5. The apparatus of claim 1, wherein the sensor further comprises a contact pressure measuring sensor configured to measure the contact pressure between the object and the sensor.

6. The apparatus of claim 5, further comprising an output interface configured to output at least one of guide information for guiding a change in the contact pressure, which is generated by the processor, and the contact pressure measured by the contact pressure measuring sensor.

7. The apparatus of claim 5, wherein the processor is further configured to generate an amplitude graph of the AC component of the bio-signal with respect to the measured contact pressure, and determine the time point, at which the amplitude of the AC component is maximum, by using the amplitude graph.

8. The apparatus of claim 5, wherein the processor is further configured to generate a slope graph of the DC component of the bio-signal with respect to the measured contact pressure, and determine the time point, at which the slope of the DC component is maximum, by using the slope graph.

9. The apparatus of claim 5, wherein the processor is further configured to determine the time point, at which the amplitude of the AC component or the slope of the DC component is maximum, with respect to the measured contact pressure that is within a reference contact pressure range, the reference contact pressure range being set for a user of the object.

10. The apparatus of claim 1, wherein the processor is further configured to extract a feature value from the bio-signal based on the determined time point, and detect the body component based on the feature value.

11. The apparatus of claim 10, wherein the feature value comprises at least one of the contact pressure, an amplitude value of the AC component, and a slope value of the DC component corresponding to the time point at which the amplitude of the AC component of the bio-signal is maximum or the time point at which the slope of the DC component of the bio-signal is maximum.

12. The apparatus of claim 1, wherein the body component comprises at least one of triglyceride, blood glucose, electrolyte, carotenoid, body water, body fat, protein, and alcohol.

13. A method of non-invasively detecting a body component, while minimizing an effect of local blood pressure, the method comprising:
    detecting a bio-signal from an object based on a contact pressure that gradually changes between the object and a sensor part;
    determining a time point at which an amplitude of an alternating current (AC) component of the bio-signal is maximum or a slope of a direct current (DC) component of the bio-signal is maximum; and
    detecting a body component based on the determined time point,
    wherein the determining the time point comprises:
    performing filtering on the bio-signal to remove noise in the contact pressure;
    differentiating the filtered bio-signal, and detecting a point having a value greater than a first predetermined threshold value, or a point having a value equal to or less than a second predetermined threshold, from the differentiated bio-signal; and
    prior to the determining the time point, removing an amplitude value of the filtered bio-signal at the detected point.

14. The method of claim 13, wherein the determining the time point comprises performing filtering on the amplitude of the AC component or the slope of the DC component, to remove outlier data.

15. The method of claim 13, wherein the determining the time point comprises, based on a detection of a plurality of time points, at which the amplitude of the AC component or the slope of the DC component in the bio-signal is greater than or equal to a predetermined threshold, correcting the amplitude of the AC component or the slope of the DC component.

16. The method of claim 15, wherein the correcting comprises correcting an amplitude value of the AC component or a slope value of the DC component by obtaining a moving average of the amplitude value of the AC component or the slope value of the DC component in units of predetermined intervals.

17. The method of claim 13, wherein the detecting the bio-signal comprises measuring the contact pressure between the object and the sensor part.

18. The method of claim 17, wherein the determining the time point comprises generating an amplitude graph of the AC component of the bio-signal with respect to the measured contact pressure, and determining the time point, at which the amplitude of the AC component is maximum, by using the amplitude graph.

19. The method of claim 18, wherein the determining the time point further comprises generating a slope graph of the DC component of the bio-signal with respect to the measured contact pressure, and determining the time point, at which the slope of the DC component is maximum, by using the slope graph.

* * * * *